United States Patent [19]

Del Masso

[11] Patent Number: Plant 6,122

[45] Date of Patent: Mar. 8, 1988

[54] PEACH TREE NAMED 'DELMASS'

[76] Inventor: Joseph Del Masso, 1723 Cottonwood La., Solvang, Calif. 93463

[21] Appl. No.: 795,106

[22] Filed: Nov. 5, 1985

[51] Int. Cl.[4] ..... A01H 5/03

[52] U.S. Cl. ..... Plt./42

[58] Field of Search ..... Plt./42

[56] References Cited

U.S. PATENT DOCUMENTS

P.P. 4,865 7/1982 Armstrong ..... Plt. 42

*Primary Examiner*—Robert E. Bagwill

[57] ABSTRACT

A peach tree having white-fleshed fruit which are firm and store well.

1 Drawing Sheet

GENERAL DATA

The origin of this peach tree is unknown, but very probably it grew from seeds of different peach varieties which were planted in my garden in the years prior to and since 1978. These were the following kinds of peaches:

a. Sims
b. Babcock
c. Wild white fleshed peach
d. White fleshed nectarines
e. Indian Red (from year to year I planted Indian Red seeds.)

There are over 100 peach trees and all of them are heavily pruned to form a bush rather than a tree, and they are crowded together to get the maximum number of trees, and for ease of cultivation and the use of drip irrigation.

This peach tree originated as a newly discovered seedling, has been asexually reproduced on my premises and it is in good health and producing peaches the same as the mother tree.

I have researched my texts on Pomology and Horticulture to determine if this variety of peach had already been discovered. I have also discussed this peach with persons in the Produce Market (Oakland, Calif.) to determine if indeed prior discovery may have occurred; there is none that I have investigated, nor am I aware of any one having asexually reproduced this peach variety, nor have I given any one any portion of this tree.

Tree is of moderate height, bark is rugose, soil condition is loam to adobe, climate is generally dry, temperature very moderate with dry, hot summers. Hardiness zone is 10.

DRAWINGS

The upper photo shows a fruit cluster, while the lower photo shows a single fruit.

SPECIFICATION

As follows:

a. Description:
b. Form of tree: no distinction can be made between this tree and the other trees.
c. Leaf characteristics: Color of upper part of leaves dark green and the bottom color of leaves is a light apple green. The Indian Red has leaves similar in size, shape, and color to this one.
   1—Leaves are lanceolate in shape.

2—Leaf thickness is comparable to others.
   3—Moderate curvature along mid-rib.
   4—The leaves of the Sims peach are a stronger yellow than this leaf.
   5—Leaf color at the end of the petiole contains light red and purple.
   6—Serration on leaf margins are medium.
   7—Pubescent buds more ovate than other peach varieties.
   8—Pigmentation of exocarp at maturity is a red purple with yellow hues.
   9—Petiole about one half inch long.
   10—One to several reniform glands of medium to large size arranged alternately.
d. Blossom characteristics:
   1—Simple flower bud.
   2—Blossoms are very small.
   3—Pale orange color.
   4—Full bloom at end of March.
   5—Blossoms start at mid-March, early compared to other peaches.
   6—Temperature variation important.
   7—Total bloom time three weeks plus or minus a few days.
e. Fruit characteristics:
   1—Immature fruit is set in latter part of March to early April.
   2—Immature fruit is sweet.
   3—Immature fruit has little acid.
   4—At maturity peach will grow over three inches in diameter.
   5—Color of new crop is ivory with faint tint of yellow and a red endocarp.
   6—Seed is of a large size and more oval than other peaches.
   7—Flesh is of melting variety.
   8—Fruit is suborbicular in shape.
   9—Pubescence is very light compared to others.
   10—Fruit is very firm.
   11—Moderately subject to brown rot, not easily bruised.
   12—Abscissions moderate to heavy.
   13—Mesocarp is ivory with a faint hue of yellow.
   14—Using the Mickel-Levy color chart the color of this peach is in the first order and the second order in the range of 536 to 600 when fully ripe having the hues of purple/violet along with patches or red/yellow.
   15—Skin easily pulled off when ripe.

16—There is little apex and suture.
17—Very difficult to separate the endocarp from the mesocarp.
18—Bears from late July through August.
19—Has good storage qualities.
20—Some tendency to oxidize.

21—Apex is less pronounced.

I do hereby claim:

1. A distinct and new variety of a plant as fully described in the above written specifications by this applicant and as shown from the color photographs.

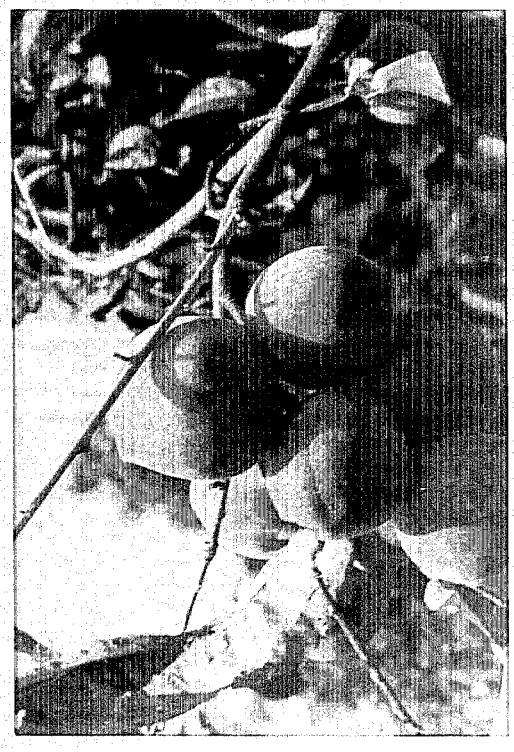
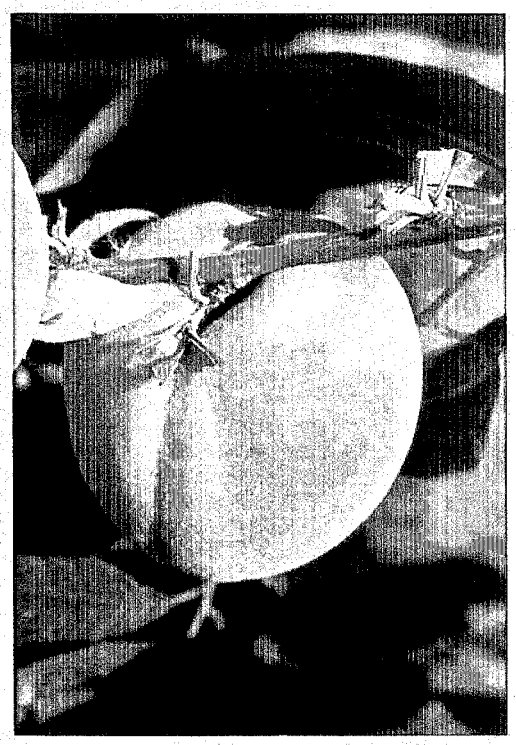

* * * * *